United States Patent [19]

Ohara et al.

[11] 4,299,541
[45] Nov. 10, 1981

[54] INFUSION SOLUTION INJECTING PUMP

[75] Inventors: Shozo Ohara; Hisakazu Sunami, both of Tokyo, Japan

[73] Assignee: Nikkiso Co., Ltd., Tokyo, Japan

[21] Appl. No.: 964,299

[22] Filed: Nov. 28, 1978

[30] Foreign Application Priority Data

Nov. 29, 1977 [JP] Japan .............................. 52/142929
Aug. 18, 1978 [JP] Japan ................................ 53/99964

[51] Int. Cl.³ .............................................. F04B 49/06
[52] U.S. Cl. ......................................... 417/12; 417/44
[58] Field of Search ....................... 417/12, 42, 44, 45, 417/474, 476, 477

[56] References Cited

U.S. PATENT DOCUMENTS

| 3,610,782 | 10/1971 | McGuire | 417/45 X |
| 3,737,251 | 6/1973 | Berman et al. | 417/477 X |
| 3,966,358 | 6/1976 | Heimes et al. | 417/45 X |
| 4,025,241 | 5/1977 | Clemens | 417/474 X |
| 4,137,011 | 1/1979 | Rock | 417/42 X |

Primary Examiner—Carlton R. Croyle
Assistant Examiner—Edward Look

[57] ABSTRACT

An infusion solution injecting pump device with the pump control means which is so arranged that various infusion patterns are stored in a memory responding to a predetermined cycle, that the cycle setting of the infusion pattern is adjustable by a convenient timer means and step control means and that the thus-programmed infusion volume data is conveniently converted into pump driving signals to control the pumping operation.

6 Claims, 12 Drawing Figures

INFUSION SOLUTION INJECTING PUMP

The invention relates to an infusion solution injecting pump device which is adapted for injection of infusion solution into a human body continuously for a predetermined period and particularly relates to a device which determines an injection volume of the infusion solution in accordance with a predetermined program for control of the pumping operation.

Hitherto, in the field of medical treatments, there have been developed and applied various injection pump of the constant trace of medicines for the purposes of medication of various medicines and nutriments, for example, nutrition for a newborn, medication of high calory infusion solution and anti-cancer medicines to cancer patients, and medication of insulin to diabetes patients.

A pump which is adapted to be used as an apparatus for medical treatment as hereinbefore described is required to be so constructed that the injection volume of infusion solutions may be varied with the passage of time to perform an infusion injecting pattern which coincides with the rhythm of the living body and that it may be conveniently carried on a human body for use in an extended period with minimum power consumption. For example, in the insulin remedy for diabetes patients the insulin is prescribed for the patients several times per day. If, however, in the remedy an insulin medication is programmable in accordance with the daily variation of the blood sugar level of the patients and moreover an insulin injection device may be carried on a human body and used continuously for a long period, the blood sugar level control performance of the medical apparatus will be considerably improved with evasion of excessive insulin medication and with assurance of social living of the patient with less constraint.

However, the conventional pumps are not provided with any control circuit and hence, whenever it is required to change the infusion volume with the passage of time, the patient has to regulate manually the infusion volume and also a specific control circuit for pumping operation is required.

The inventors, after extensive research for a purpose of overcoming the disadvantages of the conventional infusion solution injecting pump and providing a pump means which performs programmable infusion solution injecting control, have discovered that the invented pump may achieve in a simple way the desired infusion in accordance with a programmed infusion volume data when the pump control means is so arranged that various infusion patterns are stored in a memory responding to a predetermined cycle, that the cycle setting of the infusion pattern is adjustable by a convenient timer means and step control means and that the thus-programmed infusion volume data is conveniently converted into pump driving signals to control the pumping operation.

A general object of the invention is to provide an infusion solution injecting pump device in which a desired infusion pattern is stored and the pumping operation is controlled in accordance with the stored data.

A principal object of the invention is to provide an infusion solution injecting pump device which comprises a pump means connected to a driving source, a pump control means, a timer control means for setting a cycle of the infusion solution injecting pattern, a step data input means for dividing the cycle of the infusion solution injecting pattern into a plurality of steps, an input means for volume data of the infusion solution and a memory means for storing the volume data of the infusion solution and feeding said data in each step to the pump control means.

In the infusion solution injecting pump device according to the invention, the pump means is preferably constructed in such a way that an elastic tube is mounted around a revolving body with a plurality of concentrically arranged rollers or that an elastic tube is arranged between rollers and a roller guide for depression by the rollers. Also the pump means may be of a rotary pump or an infusion pump with syringe.

Another aspect of the invention is to provide a pump control means which comprises a motor and a circuit for converting the volume data signal of the infusion solution supplied from the memory means into the motor driving signals proportional to the volume data signal, wherein the converting circuit is preferably arranged to convert the volume data signal of the infusion solution into a predetermined infusion level signal. Alternatively, the converting circuit may be arranged to convert the volume data signal of the infusion solution into a predetermined infusion time rate signal. The motor may be of a D.C. motor or a pulse motor.

In the invention, the driving source for the pump means is the motor of the pump control means, which is connected to the pump means through or not through a reduction means.

Alternatively, the driving source for the pump means may be of a spring driving means which in accordance with the invention comprises a spring, a gear train for transmitting the power of the spring to a revolving body for pump driving and a governor gear connected to a portion of the gear train. The speed governor gear includes a worm and a worm gear, and the worm shaft is connected with the motor of the pump control means to perform the control of the pump means. The governor gear may be of a Geneva gear.

In a further aspect of the invention the timer means may include a timer oscillator which is operated by a start signal, a frequency converter and a frequency demultiplier, with such the arrangement that the output frequency of the timer oscillator is demultiplier into a frequency proportional to the step data for supply into the memory means.

Additionally, the step data input means is provided with an input means for setting the step data and is so arranged that the output frequency of the timer oscillator in the timer control means is converted in response to the step data signal with generation of the step signals for supplying the data stored in the memory means to the pump control means in each cycle of the infusion solution injecting pattern.

Alternatively, without predetermining the number of the step, the volume data signals delivered from the input means for setting the volume data of the infusion solution may be counted to determine the number of the ultimate input signal as the number of the step data so that the set number may be automatically provided.

The input means for volume data of infusion solution is provided with an input means for setting the volume data of the infusion solution and so arranged that the provided data of the infusion solution is supplied to the memory means.

Furthermore, the memory means includes a memory for storing the volume data of infusion solution and a data latch circuit and so arranged that the volume data signal of the infusion solution is supplied to the pump control means in response to the step signals, where the memory means may preferably use a RAM (randam access memory), a ROM (read only memory) or a magnetic tape.

One way of carrying out the invention is described in detail below with reference to drawings which illustrate only one specific embodiment, in which.

Figure 1:
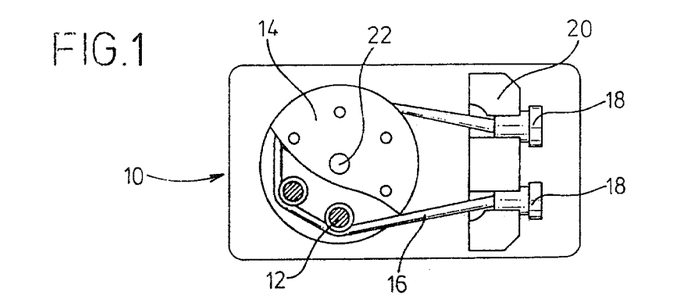
FIG. 1 is a plan view of the pumping arrangement of an infusion solution injecting pump device according to the invention.
Figure 2:
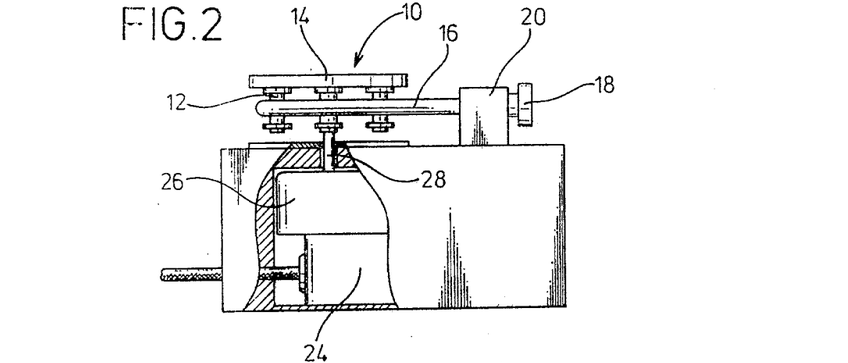
FIG. 2 is a partially sectioned lateral view of the pumping arrangement of FIG. 1.

FIGS. 1 and 2 show one embodiment of a pump means 10 of an infusion solution injecting pump device in accordance with the invention in which the pump means 10 includes a revolving body 14 with a plurality of concentrically arranged rollers 12, an elastic tube 16 mounted around the revolving body 14 and tube holder 20 adapted to hold the tube stoppers 18, 18 connected to ends of the elastic tube 16 and the shaft 22 of the revolving body 14 is conveniently connected to the driving source. Thus, the pump means 10 may be of a conventional roller pump or other pumps such as a rotary pump and an infusion pump with syringe which utilize rotary motion of the motor to perform the pumping operation.

The pump means 10 thus constructed generally includes as its driving source a motor 24 shown in FIG. 2, and an output spindle 28 of the motor 24 is connected through a convenient reduction means 26 to the turning shaft 22 of the pump means 10. The output spindle 28 of the motor 24 may be directly connected to the turning shaft 22 not through the reduction means 26 for driving the pump. A D.C. Motor or a pulse motor may preferably be used as the motor 24.

Figure 3:
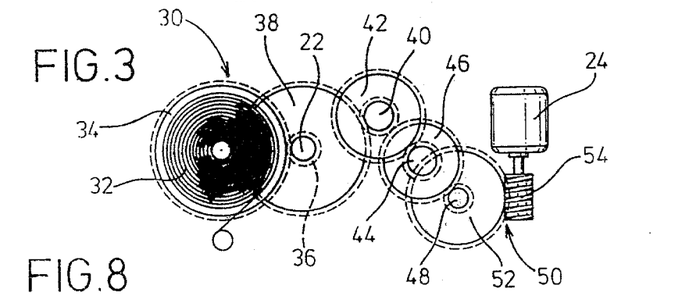
FIG. 3 is a plan view of another pump driving mechanism of the pumping arrangement of FIG. 1.

Alternatively, a spring driving means 30 as shown in FIG. 3 may also be used as a driving source for the pump means 10. This spring driving means 30 generally includes a driving spring 32, a first large gear 34 arranged coaxially with the spring 32 and connected thereto to be driven by it, a second small gear 36 arranged coaxially with the shaft 22 of the pump means 10 in mesh with the first large gear 34, a second large gear 38 arranged coaxially with the second small gear 36, on shaft 22 a third small gear 40 in mesh with the second large gear 38, a third large gear 42 arranged coaxially and fixed with the third small gear 48, a fourth small gear 44 which coacts with the third large gear 42, a fourth large gear 46 arranged coaxially and fixed with the fourth small gear 44, a fifth small gear 48 which coacts with the fourth large gear 46 and a governor gear 50 connected to the fifth small gear 48. The governor gear 50 generally includes a worm gear 52 arranged coaxially with the fifth small gear 48, a worm 54 and the motor 24 connected to the worm 54. Similarly to the embodiment shown in FIG. 2, a D.C. motor or a pulse motor may preferably be used as the motor 24, and particularly in this embodiment a small sized D.C. motor or a pulse of relatively low torque may be used as the motor 24 since the pump means 10 may be driven for a long period by the mechanical power of the spring 10. The pump shaft 22 is driven by elastic energy in the spring 32 which exerts a steady torque on gear 34 in a clockwise direction. Gear 34 meshes with small gear 36 mounted on the pump shaft 22 on which the gear 38 is also mounted. Thereby the pump shaft 22 is biased with a steady torque by the spring 32. On the other hand, since the large gear 38, also secured on the shaft 22 and is connected via gears 40-52 to the motor 24, the speed at which the shaft 22 is rotated is controlled by the speed and/or pulsing of the motor 24 which acts as a governor therefor.

When the spring driving means 30 is used, in lieu of the governor gear 50, a governor gear in which a Geneva gear is arranged coaxially with the fifth small gear 48 in engagement with a rotary plate having pins and connected to the motor 24 may be used. Moreover, use is made of a governor gear in which an escape wheel is arranged coaxially with the fifth small gear and connected through an anchor escapement to a motor which performs reversible reciprocating motion.

Figure 4:
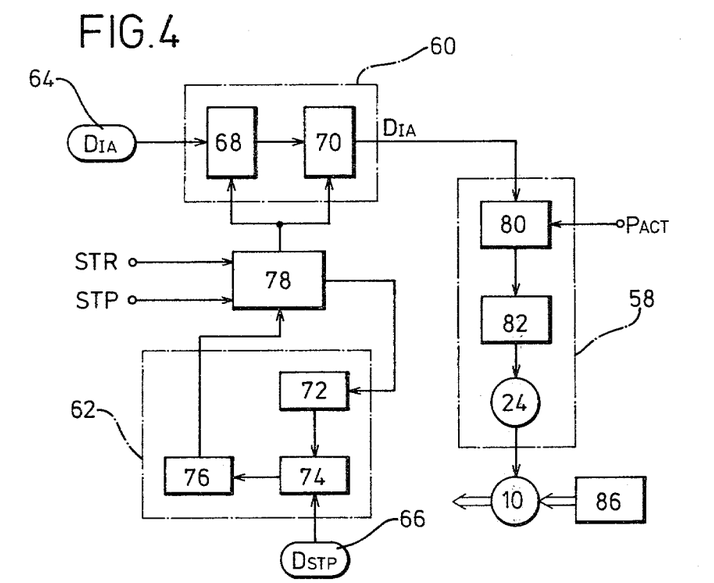
FIG. 4 is a block diagram showing an embodiment of the control circuit for controlling the pumping arrangement in accordance with the invention.

FIG. 4 shows a circuit block diagram of an embodiment of a circuit for controlling the motor 24 adapted to the pump means 10 as a driving source or a governor gear and this circuit is preferably used when a D.C. motor is applied for the motor 24. The circuit of this embodiment is essentially comprised of a pump control circuit 58, a memory circuit 60, a timer control circuit, an input means for volume data of infusion solutions 64 and a step data input means 66. The memory circuit 60 includes a memory 68 and a data latch circuit 70 and the volume data $D_{IA}$ of the infusion solution which determines the infusion solution injecting pattern and is supplied from the input means 64 for volume data of infusion solutions is stored in the memory 68 and the volume data of the infusion solution in the memory 68 is in order transmitted to the data latch circuit 70 responding to the output signal of the timer circuit 62 and in turn supplied to the pump control circuit 58 which converts the volume data $D_{IA}$ into the driving signals of a pulse motor proportional thereto. In the input means 64 for volume data of the infusion solution there is provided a convenient digital input means for setting the volume data of the infusion solution.

The timer circuit 62 includes a timer oscillator 72, a frequency converter 74 and a frequency demultiplier, and when a start signal STR is supplied through a control circuit 78 to the timer oscillator 72, the timer oscillator 72 is commenced to operate for providing the predetermined pulse signals which are supplied in turn to the frequency converter 74. The frequency converter 74 receives the step data $D_{STP}$ of the infusion solution injecting pattern supplied from the step data input means provided with a digital input means for setting steps to convert the pulse signals supplied from the timer oscillator 72 into pulse signals with a frequency proportional to the step data $D_{STP}$ and then the pulse signal is demultiplier in the frequency demultiplier and the signal obtained is supplied through the control circuit 78 to the memory circuit 60. Consequently, in the memory circuit 60, the volume data of the infusion solution stored in the memory 68 is in order transmitted to the data latch circuit responding to the demultiphied pulse signal.

Figure 5:
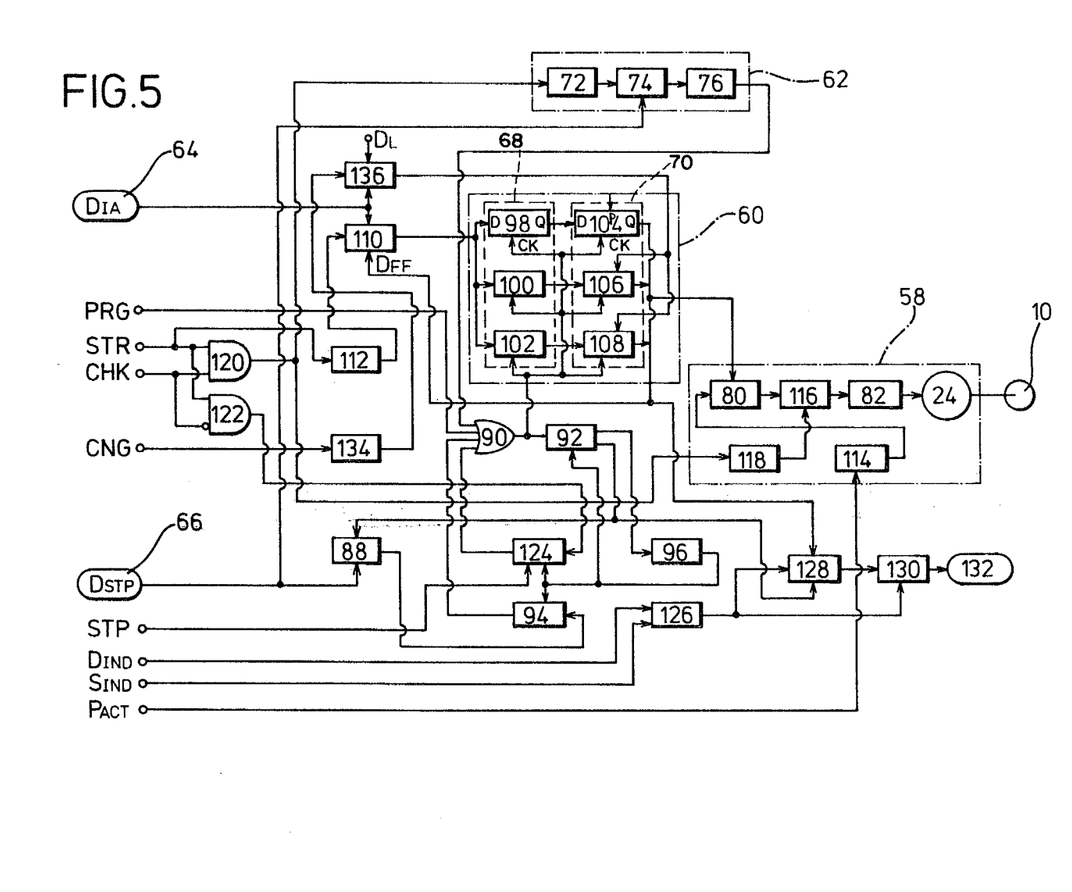
FIG. 5 is a detailed block diagram of the control circuit of FIG. 4.

The pump control circuit 58 generally includes a Degital-Analog converter 80 (hereinafter referred to as the D-A converter), an amplyfier 82 and a D.C. motor 24, where the volume data signal $D_{IA}$ of the infusion solution fed seriatim from the data latch circuit 70 of the memory circuit 60 is converted into an analog voltage signal proportional thereto. Thus the output voltage of the D-A converter 80 is applied through the amplifier 82 into the D.C. motor to drive the D.C. motor 24 so that the pump means 10 is operated to feed under the pumping operation the medical solution in the reservoir 86 conveniently connected through the piping to the pump means 10 in accordance with the volume data of the infusion solution stored in the memory circuit 60. The fine adjustment of the pump volume of infusion solution may be performed by supplying the signal $P_{ACT}$ to the D-A converter 80 for control of the reference voltage thereof. A stop signal STP is supplied to the control circuit 78 to terminate the operation of the automatic control circuit. FIG. 5 shows a further detailed circuit of the embodiment of FIG. 4. Namely, in FIG. 5, the step data input means 66 is so constructed that setting of the steps, e.g. 1 to 64 steps, may be performed and hence, when a 24 hour timer is incorporated and the step number is defined as 24, the one step corresponds to one hour. The step data $D_{STP}$ thus set is supplied to the frequency converter 74 of the timer circuit 62 and the pulse signal supplied from the timer oscillator is converted into pulse signals with frequency proportional to the step data $D_{STP}$. Also the step data $D_{STP}$ is supplied to the step comparator 88. To the step comparator 88, the data memory signal PRG which is described later in detail is supplied through the OR gate to the step counter 92 as the clock signal. Also the count signal is supplied and when the count number and the step number come coincidence with each other, the step comparator 88 supplies a signal to the step oscillator 94 to actuate the step oscillator 94.

The output of the step oscillator 94 is supplied through the OR gate to the memory circuit 60 and the step counter 92 as the clock signal for the data transmission of the memory circuit 60 and for the count advancement of the step counter 92. The step counter 92 generates a signal when the count number coinsides with the capacity number of the memory circuit 60 to actuate the step multivibrator 96 for resetting the step counter 92 and the step oscillator 94 to terminate the data transmission of the memory circuit 60.

As seen in FIG. 5, circuit 60 generally includes a memory store 68 containing a plurality of shift registers 98, 100, 102 and the data latch circuit 10 contains a plurality of flip-flops 104, 106, 108 each corresponding to each shift registers. The number of the shift register and the data latch flip-flop is determined according to the data capacity. The volume data signal $D_{IA}$ of the infusion solution supplied to the shift registers 98, 100, 102 is at first selected from the input means 64 for volume data of the infusion solution to be supplied to the data selector 110 which selects the data in accordance with the initial states of the data select flip-flop 112. In this case, the data memory signal PRG is supplied as the clock signal through the OR gate to the shift registers 98, 100, 102 and the data latch flip-flops 104, 106, 108 which store the selected volume data signal $D_{IA}$ of the infusion solution. Thus, the volume data signal $D_{IA}$ of the infusion solution is sequentially stored in the shift registers 98, 100, 102. When the number of the volume data signal $D_{IA}$ of the infusion solution comes coincidence with that of the step $D_{STP}$, the step comparator 88 operates, as described before, to shift the first program data of the shift registers 98, 100, 102 to the output until it is latched in the data latch flip-flops 104, 106, 108. Moreover, when the capacity of the shift registers 98, 100, 102 coincides with the count number of the step counter 92, the first data is latched in the shift registers 98, 100, 102 and the data latch flip-flops 104, 106, 108 and the succeeding data is stored seriatim in the shift registers 98, 100, 102. The output of the data latch flip-flops 104, 106, 108 or the first data is fed into the frequency converter 82 of the pump control circuit 58.

The pump control circuit 58 generally includes a D-C converter 80, a reference voltage generator 114 for adjusting the output voltage of the D-A converter, an amplyfier 82, an analog switch 116 connected between the D-A converter 80 and the amplifier 82, a flip-flop 118 for controlling the analog switch 116, and a D.C. motor 24. When the volume data signal $D_{IA}$ stored in the memory circuit 60 is fed into the D-A converter 80 for conversion into a D.C. voltage proportional thereto and the start signal STR is supplied through the AND gate 120 to the timer circuit 62 and to the flip-flop 118 for the analog switch, the timer control circuit is actuated while turning the flip-flop 118 into a set state and the analog switch into a ON state, so that the output voltage of the D-A converter 80 is applied through the amplifier 82 to the D.C. motor 24. Thus in the pump means 10, the revolving speed of the D.C. motor 24 is controlled proportionally to the volume data signal $D_{IA}$ of the infusion solution and the control of the pumped infusion solution volume is achieved. For the fine adjustment of the pumped infusion solution volume, a signal $P_{ACT}$ for regulating the output voltage of the reference voltage generator 114 may be supplied to the reference voltage generator 114.

In the embodiment, upon operation of the pump control circuit 58, the memory circuit 60 works such that the start signal STR directly operates the data select flip-flop 112, the output of which is fed into the data selector 110 to select the data signal $D_{FF}$ of the data latch flip-flops 104, 106, 108 in the memory circuit 60. As a result, the data signal $D_{FF}$ is sequentially fed through a route of the shift registers 98, 100, 102, the data latch flip-flops 104, 106, 108, the data selector 110 and the shift registers 98, 100, 102 and hence in the frequency converter 82 is pre-set seriatim the data signal $D_{FF}$ of the data latch flip-flops 104, 106, 108.

In the embodiment shown in FIG. 5, the circuit is so arranged that the volume data $D_{IA}$ of the infusion solution stored in the memory circuit 60 may be checked. Namely, when the stored data check signal CHK and the start signal STR are put into the AND gate 122, the output of the AND gate actuates the data check oscillator 124, the output of which is fed as the clock signal through the OR gate 90 into the memory circuit 60 and the step counter 92 so that the data $D_{FF}$ stored in the shift registers 98, 100, 102 of the memory circuit 60 travels once around the route with a slow speed of 1 to 2 seconds. At this time, when the indicating signal $D_{IND}$ of the volume data of the infusion solution is supplied through the indication gate 126 to the data selector 128, the data signal $D_{FF}$ is selected so that the content thereof may be indicated through the decoder 130 in the indicator 132.

Moreover, in the embodiment, the step number under execution may be indicated for confirmation thereof. In this case, if the output of the step counter 92 is supplied to the data selector 128 and the step data indicating signal $S_{IND}$ is fed through the indication gate 126 into the data selector 128, the step data signal is selected so that the content thereof may be indicated through the decoder 130 in the indicator 132.

In the checking operation of the memory circuit 60, when any difference between the value of the indicator 132 and the program data sheet arised, the stop signal STP is fed into the data check oscillator 124 to terminate the operation thereof and then the error memory data correction signal CNG is fed into the data change multivibrator 134, the output of which is supplied to the data selector 136 for correction so that the correct volume data $D_{IA}$ of the infusion solution is selected in the data selector 136 for correction for pre-setting in the data latch flip-flops 104, 106, 108 for correction of the stored content of the volume data of the infusion solution. Usually the data selector 136 is supplied with a Zero signal $D_L$ and produces the pre-set signal only when any input is supplied from the data change multivibrator. After completion of the check of the stored data in the memory circuit 60, the supply of the memory check signal CHK is terminated and the start signal only is fed before the AND gate 120 generates the output signals for starting the operation of the pump control circuit 58.

In the embodiment hereinbefore described, the open-loop type revolving speed control is employed for controlling the D.C. motor 24. However, in order to achieve more precise infusion, a feedback loop type control may be adopted so as to realize the phase control or the revolving speed control utilizing the reverse electromotive force of the D.C. motor. The device according to invention may also be so constructed that more than two kinds of infusion injecting patterns are in advance stored in the read-only-memory for sequential selection with a convenient micro computer without however setting sequentially the volume data $D_{IA}$ of the infusion solution in the memory circuit 60.

Figure 6:
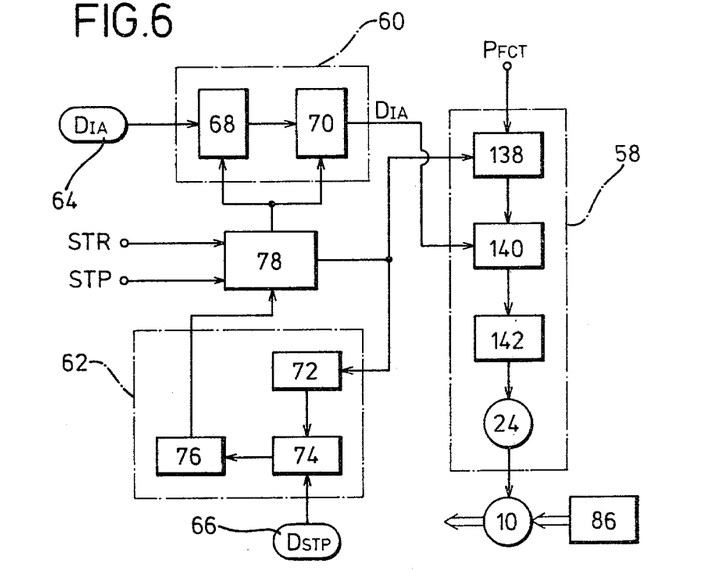
FIG. 6 is a block diagram showing another embodiment of the control circuit for controlling the pumping arrangement in accordance with the invention.

FIG. 6 shows another embodiment of the control circuit shown in FIGS. 4 and 5, and the control circuit is preferably used for the pump device including as a motor 24 a pulse motor. The circuit of this embodiment as compared with that shown in FIG. 4 is only different in the pump control circuit 58 and the other circuit arrangements and functions thereof are quite the same.

In FIG. 6, the pump control circuit 58 includes a pump oscillator 138, a frequency converter 140, a logic circuit 142 for driving the pulse motor and a pulse motor 24, and when a start signal is supplied through the control circuit 78 to the pump oscillator 138, the pump oscillator 138 operates to supply a predetermined output signal to the frequency converter 140 which in turn receives the volume data $D_{IA}$ of the infusion solution supplied seriatim from the data latch circuit 70 of the memory circuit 60 to convert the frequency of the signal proportionally to the data for supply to the logic circuit 142 for driving the pulse motor. Thus, the pulse motor 24 is driven responding to the output signal from the logic circuit 142 for driving the pulse motor.

Figure 7:
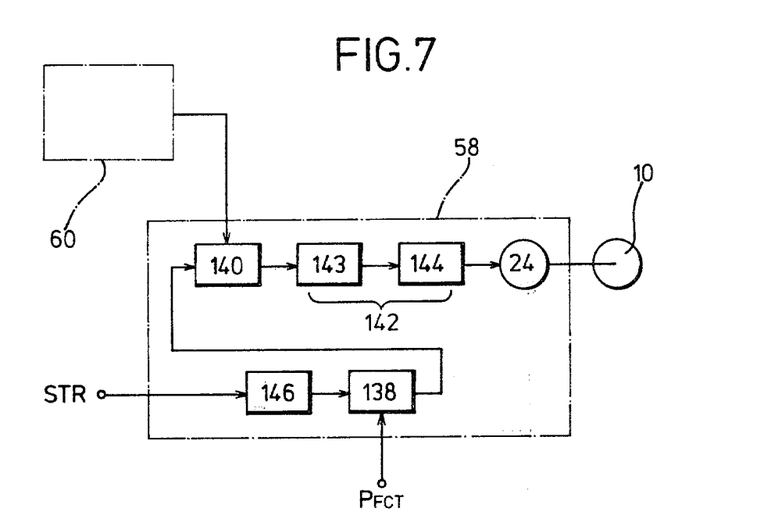
FIG. 7 is a detailed block diagram of the pump control circuit of FIG. 6.

Alternatively, the control circuit shown in FIG. 5 may be employed to the embodiment of FIG. 6 without any change, where the pump control circuit 58 is constructed as shown in FIG. 7 in which the pump control circuit 58 is provided with the logic circuit 142 for driving the pulse motor including a pulse motor controller 143 and a pulse motor driver 144 connected with each other and the pump oscillator 138 is provided with a pump oscillator flip-flop 146 when the start signal STR is supplied through the AND gate 120 to the timer means circuit 62 and the pump oscillator flip-flop 146, the timer circuit 62 oerates and at the same time the pump oscillator flip-flop 146 is set to actuate the pump oscillator 138. The output signal of the pump oscillator 138 is fed into the frequency converter 140 for conversion into a frequency proportional to the data signal $D_{FF}$ supplied through the data latch flip-flop of the memory circuit 60. The output signal thus obtained in the frequency converter 140 is further converted in the pulse motor controller 143 into a train of pulses required for driving the pulse motor to drive the pulse motor 24 through the pulse driver 144 with operation of the pump means 10. For the fine adjustment of the pumped infusion solution volume, a signal $P_{FCT}$ for regulating the oscillation frequency of the pump oscillator 138 may be fed into the pump oscillator 138.

Figures 8, 8A, 8B:
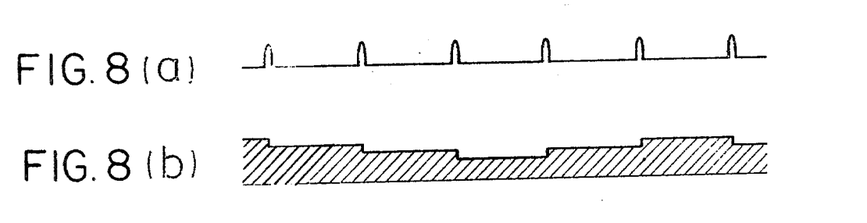
FIG. 8 shows wave forms of the infusion solution injecting pattern in the pump means controlled by the control circuits shown in FIGS. 4 to 7.

According to the embodiments shown in FIGS. 4 to 7, the control of the infusion solution volume in the pump means 10 may be performed by controlling the variation of the infusion solution level as shown in FIG. 8b which varies in each step in accordance with the output signal as shown in FIG. 8a of the demultiplier in the timer circuit 62 and the infusion which is controlled according to the patient's physiological change may be performed under the continuous operation of the pump 10.

Figure 9:
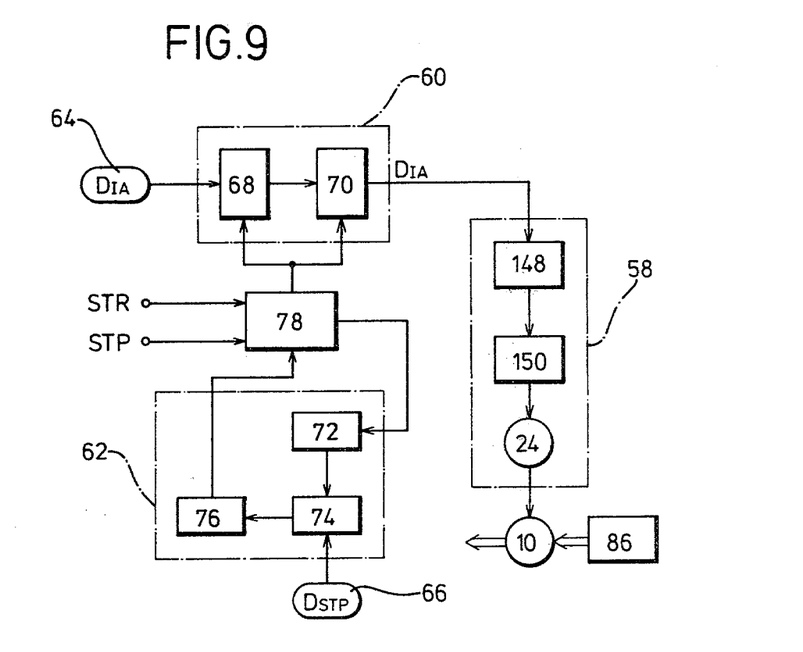
FIG. 9 is a block diagram showing another embodiment of a control circuit for controlling the pumping arrangement of the invention.

FIG. 9 shows another embodiment of the control circuit for a D.C. motor where the pump control circuit 58 includes a chopper oscillator 148, a chopper amplifier 150 and a D.C. motor. In the embodiment, the volume data $D_{IA}$ of the infusion solution stored in the memory circuit 60 is fed into the chopper oscillator 148 for conversion into a train of pulses with a duty ratio proportional to the volume data and then the train of pulses is fed into the chopper oscillator 150 to obtain an average voltage which is proportional to the train of pulses with a predetermined duty ratio and the average voltage thus obtained is in turn applied to the D.C. motor 24 to control the revolving speed of the D.C. motor.

Figure 10:
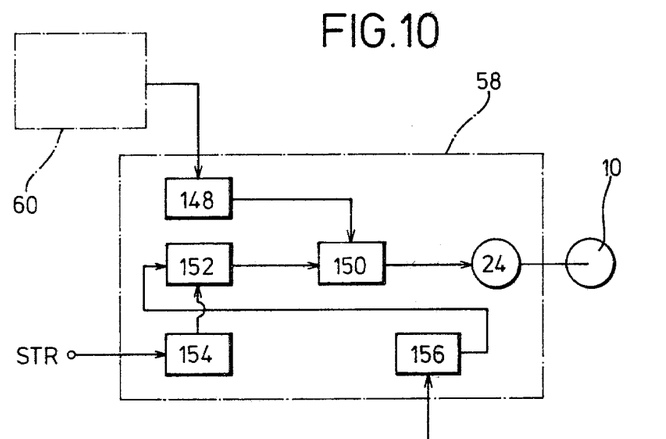
FIG. 10 is a detailed block diagram of the pump control circuit as shown in FIG. 9.

The control circuit shown in FIG. 5 may be used in the embodiment similarly to the embodiment shown in FIG. 9. Hence, when the embodiment shown in FIG. 9 is employed for the control circuit shown in FIG. 5 the pump control circuit 58 is constructed as shown in FIG. 10 in which the pump control circuit 58 includes a chopper oscillator 148, a chopper amplifier 150, an analog switch 152 for controlling the operation of the chopper amplifier 150, a flip-flop 154 for the analog switch for controlling the analog switch 152, a D.C. voltage generator 156 for ajusting the operation of the analog switch and a D.C. motor.

The volume data $D_{IA}$ of the infusion solution stored in the memory circuit 60 is supplied to the chopper oscillator 48 for conversion into a train of pulses with a duty ratio proportional thereto and then the start signal STR is fed into the flip-flop 154 for the analog switch to make the flip-flop 154 turn into the set state and also make the analog switch 152 turn into the ON-state, so that the chopper amplifier 150 operates to convert in the chopper amplifier the train of output pulses of the chopper oscillator into a train of pulses with a predetermined voltage for driving the D.C. motor, the average voltage of which is applied to the D.C. motor 24. Thus, the pump means 10 may achieve the control of the pumped infusion solution volume. Moreover, for the fine adjustment of the pumped infusion solution volume in the embodiment, the signal $P_{CCT}$ which regulates an output voltage of the D.C. voltage generator 156 may be supplied to the reference voltage generator 156.

Figure 11:
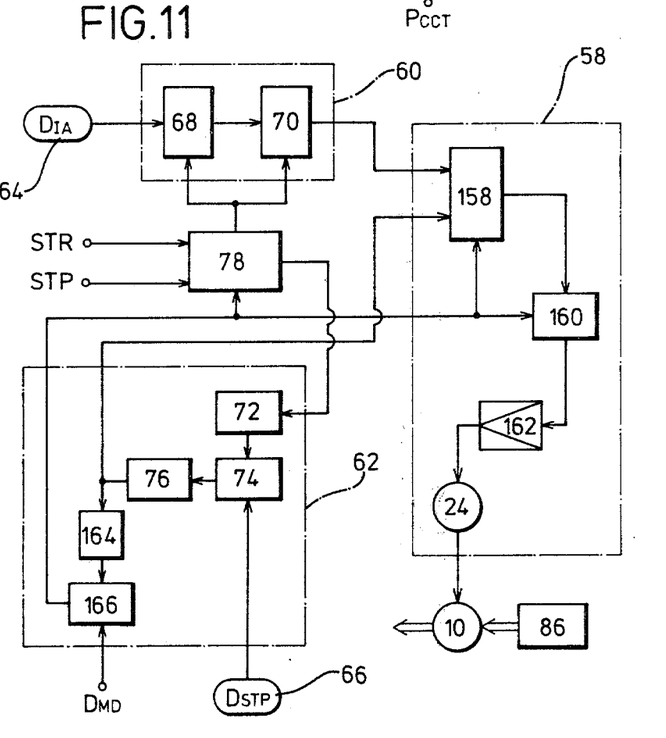
FIG. 11 is a block diagram showing further another embodiment of a control circuit for controlling the pumping arrangement of the invention.

FIG. 11 shows a further embodiment of the control circuit for a D.C. motor 24 in which the pump control circuit 58 includes an up-down counter 158, a flip-flop 160, an amplifier 162 and a D.C. motor. In the embodiment, the volume data $D_{IA}$ of the infusion solution stored in the memory circuit 60 is fed into the up-down counter 158 to preset the same while setting the flip-flop 160 so as to perform the substraction by the up-down counter 158 with the signals supplied from the timer circuit 62 and when the content of the up-down counter 158 reaches zero the flip-flop 160 is reset and the output of the flip-flop 160 is applied as a driving voltage to the D.C. motor 24 through the amplifier 162 for operation of the D.C. motor while the flip-flop 160 is reset. Moreover, in the embodiment the timer circuit 62 is provided with a counter 164 and a comparator 166 to which the signal $D_{MD}$ for setting the maximum value of the infusion pattern is fed and the output of the demultiplier in the timer circuit 62 is supplied through the counter 164 to the comparator 166 so that the efficiency per the driving hour of the D.C. motor is enhanced by the maximum setting value signal $D_{MD}$ without changing the time per one step to be determined by the step data and that the output of the demultiplier is supplied to the up-down counter 158 as the operation signal.

Figure 12:
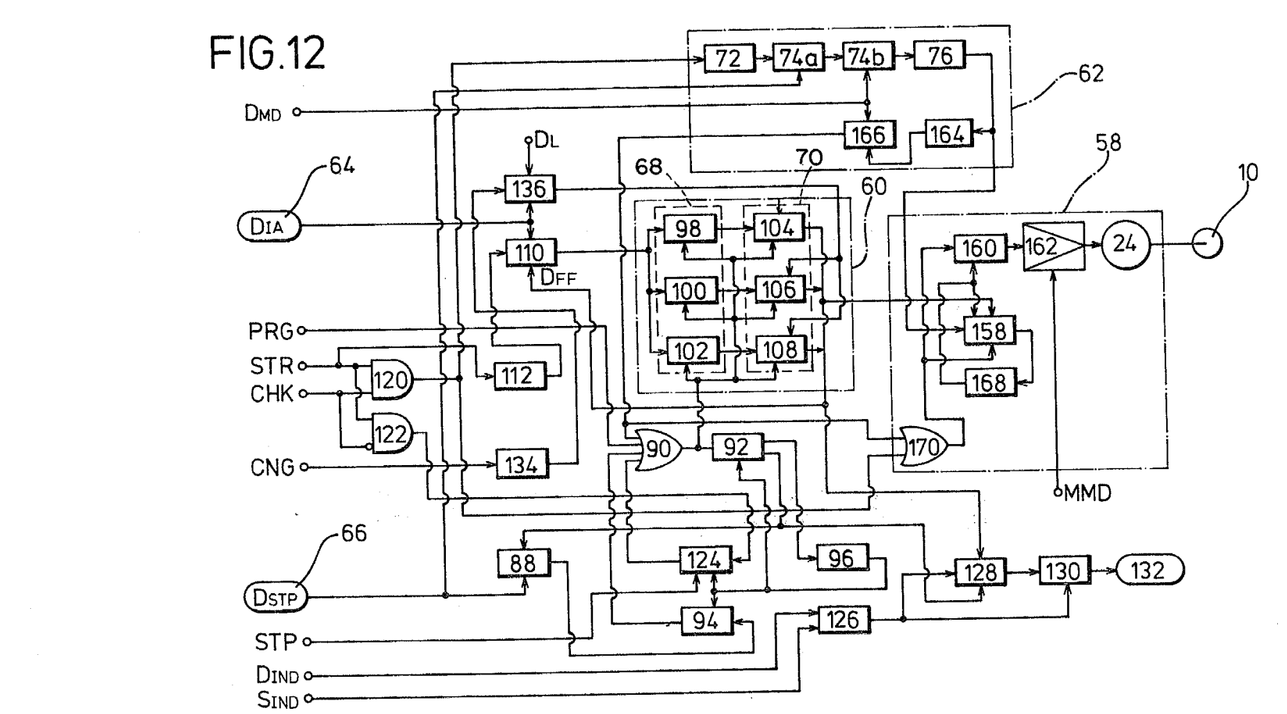
FIG. 12 is a detailed block diagram of the pump control circuit as shown in FIG. 11.

FIG. 12 shows a further detailed circuit diagram of the embodiment shown in FIG. 11. The circuit shown in FIG. 12 is quite similar to that of FIG. 5 in the arrangement and functions except the pump control circuit 58 differ the timer control circuit 62 differ. Accordingly, the corresponding similar parts are designated by the same reference numbers for elimination of the duplicate description.

In FIG. 12, the timer control circuit 62 is comprised of a timer oscillator 72, a first frequency converter 74a, a second frequency converter 74b, a demultiplier, a decimal counter 164 and a comparator 166, and the timer oscillator 72 is energized by the start signal STR and the output signal of the timer oscillator 72 is converted in its frequency in the first frequency converter 74a on the basis of the step data signal $D_{STP}$ and further converted in its frequency in the second frequency converter 74b by the signal $D_{MD}$ for setting the maximum value of the infusion pattern before the frequency thereof is demultiplied in the demultiplier 76. The output of the demultiplier 76 is further supplied through the decimal counter 164 to the comparator 166 so that the efficiency per a driving hour of the D.C. motor is enhanced by the maximum setting value signal $D_{MD}$ without changing the time per one step to be determined by the step data and the output signal of the comparator 166 is fed to the memory circuit 60 as a data transfer signal.

The pump control circuit 58 includes a subtraction counter 158, a flip-flop 160, an amplifier 162, a mono-multivibrator 168, an OR gate 170, and a D.C. motor in which the start signal STR is supplied through the AND gate 120 to the OR gate 170 the output of which turns the flip-flop 160 into the ON state for pre-setting the subtraction counter 158 with the volume data $D_{IA}$ of the infusion solution stored in the memory circuit 60. Also the subtraction counter 158 is supplied with a clock signal of the output of the demultiplier in the timer circuit 62 for executing the subtraction until all of the contents in the subtraction counter 158 become zero, when the carrier signal is produced to operate the multivibrator 168 for resetting the flip-flop 160 and the subtraction counter 158. At this time, the output voltage of the flip-flop is applied to the amplifier 162 to be amplified and then applied to the D.C. motor. Thus, in the embodiment, the volume data signal of the infusion solution is converted into a motor driving signal with a time rate proportional thereto to control the driving of the D.C. motor 24 for controlling the pumped volume of the infusion solution. In the embodiment, the pump means 10 may be manually controlled by supplying a manual operation signal MMD to the amplifier 162 in the pump control circuit 58.

According to the invention, there may be readily provided a small-sized, portable, artificial kidney device with high performance which enables the blood sugar level control repeated in a predetermined cycle since the device, for example, is so constructed that the quantity of insulin to be injected is programmed for a predetermined period in accordance with the variation pattern of the blood sugar level of the diabetes patients.

Further, in accordance with the device of the present invention, the check and the correction of the stored data of the infusion solution volume are so easy that the device is remakably convenient for health control of the patient. Moreover, the device may be so constructed that the infusion solution volume data is stored in advance in the read-only-storage, whereas the predetermined infusion solution volume data is sequentially set in the memory.

Further in the device according to the invention, when the driving of the pump portion is performed by the mechanical power of the spring, the output control of the infusion solution in the pump means could be executed by a small-sized motor with a low output, so that the electric source of a small-sized dry cell may be used for a longer time and the automatic control circuit is reduced in size by using an integrated circuit. Moreover, the spring driving mechanism may be reduced in size with a greater output power by utilizing the convenient watch mechanism and hence there is provided a small-sized pump device for injection of a trace of the solution which is conveniently brought about by the patient.

While the invention is described in connection with the preferred embodiment, various modification and change may be made without departing from the spirit of the invention.

We claim:

1. An infusion solution injecting pump device comprising pump means, timer control means, step data input means, memory means, volume data input means, and pump control means, said volume data input means supplying solution infusion volume data to said memory means for storage, said memory means including shift registers for storage of said solution infusion volume data and a data latch circuit, said step data input means providing a step data signal of solution infusion pattern to said timer control means as a controlling signal, said timer control means including a timer oscillator for generating a given timer signal, a frequency converter for converting said timer signal into a pulse signal having a frequency proportional to the step data and a frequency demultiplier for demultiplying the frequency of the pulse signal, said memory means transmitting the volume data stored in the memory successively to the data latch circuit under the controlling signal from the timer control signal cooperating with said controlling signal to supply said volume data to said pump control means in the event the injecting volume of said pump changes, said pump control means including a motor and said pump control means converting volume data signal into a motor driving signal, and said timer control means and said pump control means responding to start and stop signals in the device.

2. The device in accordance with claim 1, wherein said pump control means includes a converting circuit for converting said volume data signal into a predetermined infusion level signal.

3. The device in accordance with claim 1, wherein said pump control means includes a converting circuit for converting said volume data signal into a predetermined infusion time rate signal.

4. The device in accordance with claim 1, wherein said pump control means includes spring driving means for transmitting spring tension to a revolving body of said pump means, and further comprising a gear train and a governor gear for controlling the rotation rate of said revolving body, said governor gear being connected to a driving shaft of said motor of said pump control means.

5. The device in accordance with claim 4, wherein said governor gear includes a worm and a worm gear, and further including a worm gear shaft connected to said motor selectively through reduction means.

6. The device in accordance with claim 4, wherein said governor gear comprises a Geneva gear having a plurality of grooves, said gear partially engaging a revolving means, said revolving means being connected with said motor selectively through a reduction means.

* * * * *